(12) United States Patent
Mera et al.

(10) Patent No.: US 12,382,957 B2
(45) Date of Patent: Aug. 12, 2025

(54) LACTAM COMPOUND OR SALT THEREOF, COMPLEX, AND FERTILIZER AND PLANT GROWTH REGULATOR CONTAINING SAID COMPOUND OR SALT AND COMPLEX

(71) Applicants: AICHI STEEL CORPORATION, Tokai (JP); TOKUSHIMA UNIVERSITY, Tokushima (JP)

(72) Inventors: Akane Mera, Tokai (JP); Motofumi Suzuki, Tokai (JP); Kensuke Hosoda, Tokai (JP); Kosuke Namba, Tokushima (JP)

(73) Assignees: AICHI STEEL CORPORATION, Tokai (JP); TOKUSHIMA UNIVERSITY, Tokushima (JP)

( * ) Notice: Subject to any disclaimer, the term of this patent is extended or adjusted under 35 U.S.C. 154(b) by 536 days.

(21) Appl. No.: 17/905,238

(22) PCT Filed: Dec. 10, 2020

(86) PCT No.: PCT/JP2020/046166
§ 371 (c)(1),
(2) Date: Aug. 29, 2022

(87) PCT Pub. No.: WO2021/199507
PCT Pub. Date: Oct. 7, 2021

(65) Prior Publication Data
US 2023/0137078 A1    May 4, 2023

(30) Foreign Application Priority Data
Mar. 30, 2020   (JP) .................. 2020-060320

(51) Int. Cl.
| | |
|---|---|
| *A01N 43/36* | (2006.01) |
| *A01P 21/00* | (2006.01) |
| *C05C 11/00* | (2006.01) |
| *C07D 207/273* | (2006.01) |
| *C07F 15/02* | (2006.01) |

(52) U.S. Cl.
CPC .............. *A01N 43/36* (2013.01); *A01P 21/00* (2021.08); *C05C 11/00* (2013.01); *C07D 207/273* (2013.01); *C07F 15/02* (2013.01)

(58) Field of Classification Search
CPC ...... C07D 207/273; A01N 43/36; A01P 21/00
See application file for complete search history.

(56) References Cited

U.S. PATENT DOCUMENTS 2,578,526 A    12/1951   Evans et al.

FOREIGN PATENT DOCUMENTS

| CN | 108863580 A | 11/2018 |
| JP | 2017-60426 A | 3/2017 |
| JP | 2017-226548 A | 12/2018 |
| WO | WO2020045247 | 3/2020 |

OTHER PUBLICATIONS

Combined Canadian Office Action and Search Report issued Nov. 20, 2024, received Jan. 7, 2025, in Canadian Patent Application No. 3,170,213, 4 pages.
International Search Report mailed on Jan. 26, 2021 in PCT/JP2020/046166 filed on Dec. 10, 2020 (2 pages).
Combined Chinese Office Action and Search Report issued Aug. 30, 2023 in Chinese Application 202080095557.1 (with unedited computer-generated English translation), 10 pages.
Office Action received dated Apr. 30, 2025.in the corresponding Brazilian application No. 112022015131-4 (with English translation), citing document 15 therein.

*Primary Examiner* — Kamal A Saeed
(74) *Attorney, Agent, or Firm* — Oblon, McClelland, Maier & Neustadt, L.L.P.

(57) ABSTRACT

A lactam compound and a salt thereof, represented by general formulae (1) and (2):

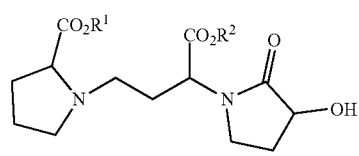

(1)

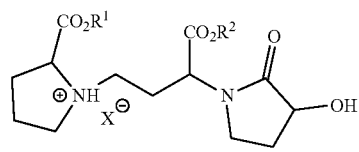

(2)

In the formulae, $R^1$ and $R^2$ may be the same or different, and each represent a hydrogen atom, a protective group of a carboxyl group or a cation, and $X^-$ is a halogen ion, an organic acid ion, or an inorganic acid ion.

8 Claims, 4 Drawing Sheets

LACTAM COMPOUND OR SALT THEREOF, COMPLEX, AND FERTILIZER AND PLANT GROWTH REGULATOR CONTAINING SAID COMPOUND OR SALT AND COMPLEX

CROSS REFERENCE TO RELATED APPLICATIONS

This application is a National Stage entry under 35 U.S.C. § 371 of PCT/JP2020/046166, filed on Dec. 10, 2020, and claims priority to Japanese Patent Application No. 2020-060320, filed on Mar. 30, 2020 the entire contents of which are incorporated herein by reference.

FIELD OF THE INVENTION

The present invention relates to a compound that has a metal uptake ability and is suitable as an iron supply material for cultivation using foliar spraying and hydroponics when used as an iron complex; a complex; and a fertilizer and a plant growth regulator that contain the compound or the complex, and are used for plant growth.

BACKGROUND ART

Conventionally, hydroponics is less affected by the season, weather, or the like, and allows for stable cultivation, and is therefore widely used as a plant cultivation method. Hydroponics is a method of cultivating plants using nutrients from a culture medium (fertilizers) without using soil. A variety of fertilizers are used in hydroponics, and an organic fertilizer containing boiled water obtained in the production process of dried bonito, or an iron compound such as iron chelate of ethylenediaminetetraacetic acid (hereinafter, referred to as "Fe-EDTA"), iron chloride, iron sulfate, and iron pyrophosphate described in Patent Literature 1 is used.

There is a foliar spraying method with chemicals as another method for plant cultivation, because it improves productivity, quality, and the like. Biologically active substances, and liquid fertilizers containing fine powdered seaweed described in Patent Literature 2 are known as the chemicals.

PRIOR ART LITERATURE

Patent Literature

Patent Literature 1: JP-A 2017-60426
Patent Literature 2: JP-A 2017-226548

SUMMARY OF THE INVENTION

Problems that the Invention is to Solve

The problem of the present invention is to provide a compound which has a metal uptake ability and is suitable as an iron supply material for cultivation using foliar spraying and hydroponics when used as an iron complex; a complex; and a fertilizer and a plant growth regulator containing these.

Means for Solving the Problems

The present invention is as follows.
[1] A lactam compound and a salt thereof, represented by general formulae (1) and (2).

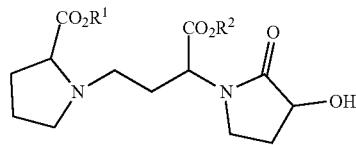

(1)

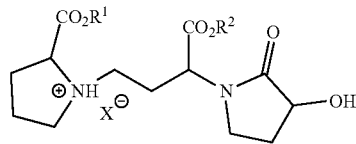

(2)

(In the formulae, $R^1$ and $R^2$ may be the same or different, and each represent a hydrogen atom, a protective group of a carboxyl group, or a cation, and $X^-$ is a halogen ion, an organic acid ion, or an inorganic acid ion.)

[2] The lactam compound and a salt thereof according to [1] above, wherein $R^1$ and $R^2$ in the general formulae (1) and (2) are hydrogen atoms.

[3] The lactam compound and a salt thereof according to [1] above, wherein $R^1$ and $R^2$ in the general formulae (1) and (2) are protective groups of a carboxyl group, and the protective group is a methyl group or an ethyl group.

[4] The lactam compound and a salt thereof according to [1] above, which is represented by general formulae (1A) and (2A):

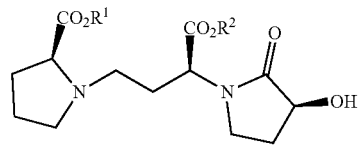

(1A)

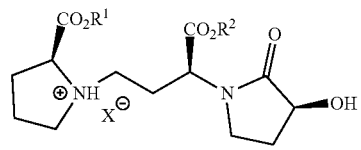

(2A)

(In the formulae, $R^1$ and $R^2$ may be the same or different, and each represent a hydrogen atom, a protective group of a carboxyl group, or a cation, and $X^-$ is a halogen ion, an organic acid ion, or an inorganic acid ion.)

[5] A complex comprising the lactam compound or salt thereof according to any one of [1] to [4] above, and a metal atom.

[6] The complex according to [5] above, wherein the metal atom is an iron.

[7] A fertilizer comprising the lactam compound or salt thereof according to any one of [1] to [4] above, or the complex according to [5] or [6] above.

[8] A plant growth regulating agent comprising the lactam compound or salt thereof according to any one of [1] to [4] above, or the complex according to [5] or [6] above.

Effects of the Invention

In the present invention, the lactam compound and salt represented by the general formulae (1) and (2) are stable in a pH range from 1 to 9 since opening of the lactam ring is not occurred, and the compounds easily form metal complexes. For example, when an iron complex is prepared, it is suitable as an iron supply material for cultivation using foliar spraying and hydroponics. The lactam compounds of the present invention are also suitable for plant growth in alkaline soils when used alone or in combination with a divalent or trivalent iron compound. Therefore, the lactam compound and salt of the present invention, and complex of the present invention are suitable as a raw material component for a fertilizer or a plant growth regulator.

EMBODIMENT FOR CARRYING OUT THE INVENTION

Figure 1:
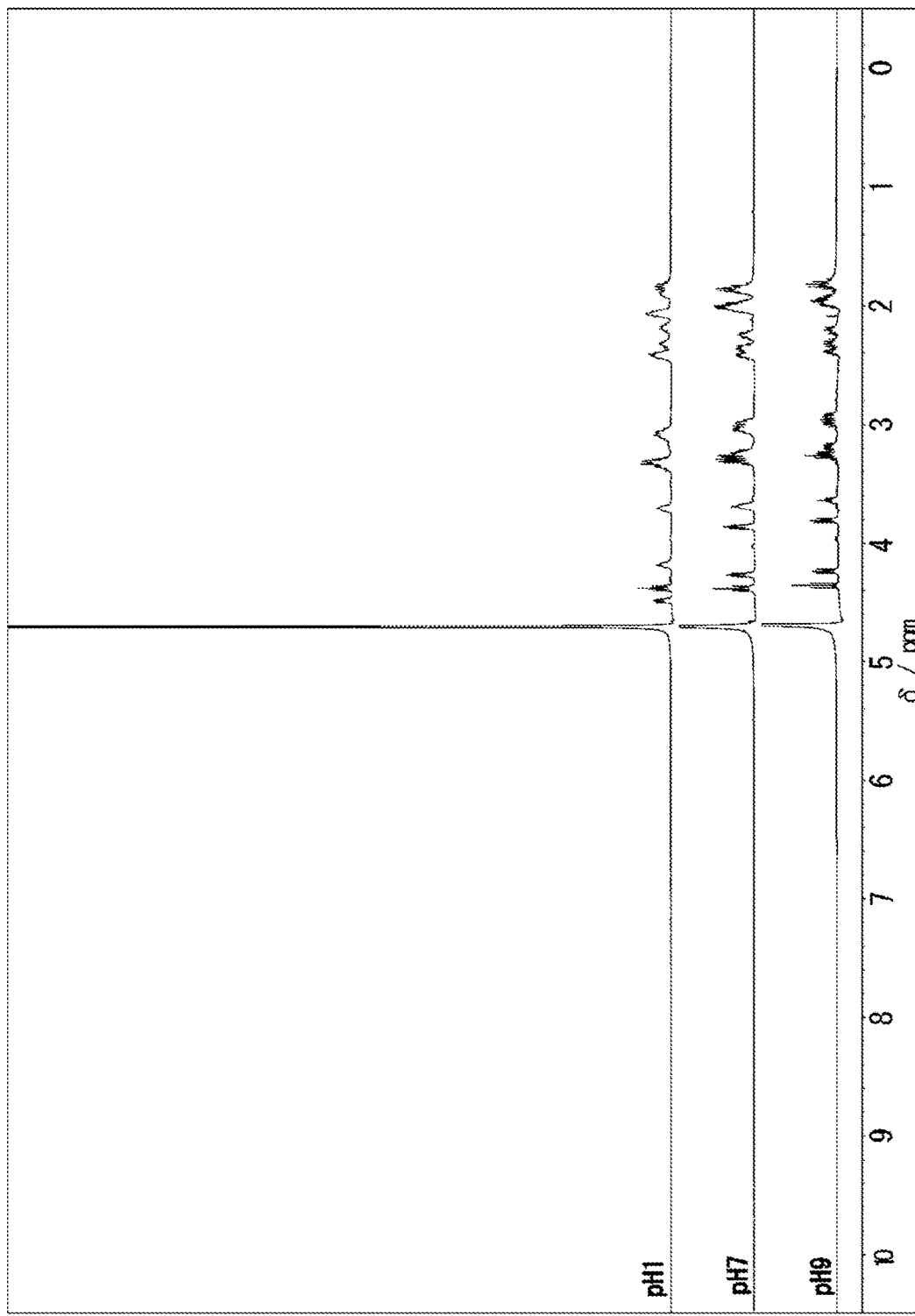
FIG. 1 is a $^1$H-NMR spectra of the lactam compound (L2) obtained in Example 1, showing results of the stability test in waters with different pH.

The lactam compound or the salt thereof are represented by the following general formulae (1) and (2). The compound of the general formula (2) is a salt of the compound of the general formula (1).

ethyl group, and pivaloyloxymethyl group; and the like. Among these, methyl group and ethyl group are preferable.

It is noted that "n-" means normal; "iso-" means iso; "tert-" means tertiary; "o-" means ortho; "m-" means meta; and "p-" means para.

In case where $R^1$ and $R^2$ are cations, the cation may be either an inorganic cation or an organic cation. Examples of the inorganic cation include $NH_4^+$, $Na^+$, $K^+$, $Ag^+$, and the like.

$X^-$ in the general formula (2) is a halogen ion, an organic acid ion, or an inorganic acid ion, and may be, for example, a halogen ion such as a chlorine ion, a bromine ion and an iodine ion; acetic acid ion, trifluoroacetic acid ion, methanesulfonic acid ion, nitric acid ion, sulfate ion, and the like. Of these, chlorine ion, nitrate ion, sulfate ion, and trifluoroacetate ion are preferred.

The salt represented by the general formula (2) is not particularly limited, and example thereof includes an inorganic acid salt such as a hydrochloride, a sulfate, and a nitrate; an organic acid salt such as an acetate, and a methanesulfonate; an alkali metal salt such as a sodium salt, and a potassium salt; an alkaline earth metal salt such as a magnesium salt, and a calcium salt; a quaternary ammonium salt such as a dimethylammonium salt, and a triethylammonium salt; and the like. These salts are suitable in the agricultural field.

In the present invention, particularly preferred embodiments as a raw material component for a fertilizer or plant growth regulator include a lactam compound or salt thereof wherein both $R^1$ and $R^2$ in the general formulae (1) and (2) are hydrogen atoms and are represented by the following formulae (3) and (4).

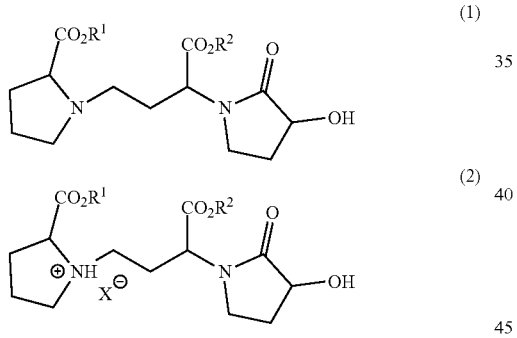

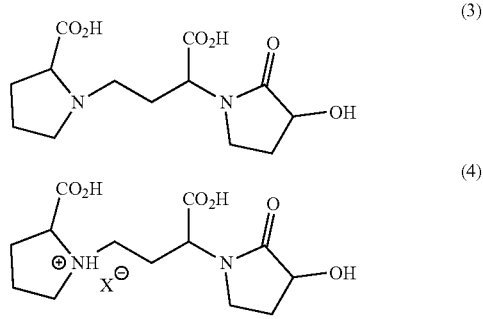

(In the formulae, $R^1$ and $R^2$ may be the same or different, and each represent a hydrogen atom, a protective group of a carboxyl group, or a cation, and $X^-$ is a halogen ion, an organic acid ion, or an inorganic acid ion.)

In the general formulae (1) and (2), $R^1$ and $R^2$ may be the same or different, and each represent a hydrogen atom, a protective group of a carboxyl group or a cation.

When $R^1$ and $R^2$ are protecting groups of a carboxyl group, the protecting group is not particularly limited, and example thereof includes a linear, branched or cyclic alkyl group having 1-6 carbon atoms, such as methyl group, ethyl group, n-propyl group, iso-propyl group, n-butyl group, iso-butyl group, tert-butyl group, n-hexyl group, and cyclohexyl group; an aralkyl group which may have a substituent, such as benzyl group, p-nitrobenzyl group, o-nitrobenzyl group, m-nitrobenzyl group, 2,4-dinitrobenzyl group, p-chlorobenzyl group, p-bromobenzyl group, and p-methoxybenzyl group; an alkylcarbonyloxy-alkyl group, the alkylcarbonyloxy having 1 to 6 carbon atoms, such as acetoxymethyl group, acetoxyethyl group, propionyloxymethyl group, n-butyryloxymethyl group, iso-butyryloxym- (In the formulae, $X^-$ is a halogen ion, an organic acid ion, or an inorganic acid ion.)

The lactam compound and salt thereof in the present invention may have an isomer such as optical isomers, stereoisomers and position isomers. For example, when the lactam compound and salt thereof have optical isomers, optical isomers divided from a racemic body are also included in the compound of the present invention.

The preferred optical isomers as the lactam compound and salt thereof in the present invention are the following compounds represented by general formulae (1A) and (2A). In these formulae, $R^1$, $R^2$ and $X^-$ are as described above.

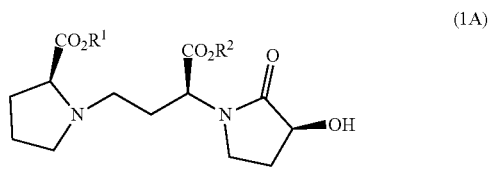

-continued

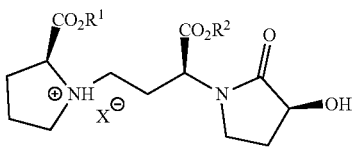

(2A)

The production method of the lactam compound and salt thereof in the present invention is not particularly limited.

Compounds where $R^1$ and $R^2$ are hydrogen atoms in the above formulae (1) and (2) may be produced by the following methods. For example, the compound represented by the above formula (4) may be produced by dissolving in an aqueous solution of dilute hydrochloric acid a compound represented by the following formula (6), obtained by the method described in WO2017/082111, subjecting the solution to concentration to form a hydrochloride salt of a compound represented by the following formula (6), and then heating the hydrochloride salt at a temperature from 40° C. to 100° C. The compound represented by the above formula (3) may be produced by subjecting the resulting compound represented by the above formula (4) to cation exchange.

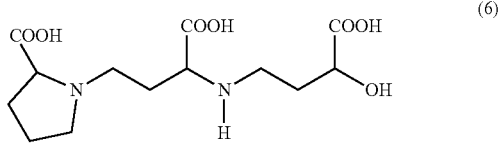 [SMILES: O=C(O)C(O)CCNC(CCN1CCCC1C(=O)O)C(=O)O]

(6)

Compounds in which $R^1$ and $R^2$ are protecting groups of a carboxyl group, e.g., methyl groups, in the above general formula (2) may be produced by adding the compound represented by the above formula (3) to anhydrous hydrochloric acid-methanol solution, stirring them, and subjecting the resulting reaction solution to concentration. In a case where $R^1$ and $R^2$ are ethyl groups, ethanol may be used.

Further, compounds in which $R^1$ and $R^2$ are cations (e.g., $NH_4^+$) in the above general formula (1) may be produced by adding the compound represented by the above formula (3) to aqueous ammonia, stirring them, and subjecting the resulting reaction solution to concentration. In a case where $R^1$ and $R^2$ are $Na^+$ ions, an aqueous solution of sodium hydroxide may be used.

In the present invention, a complex may be produced by mixing an aqueous solution of a lactam compound or salt thereof with an aqueous solution containing a metal ion. Each of the above aqueous solutions may be obtained using water or a buffer solution. The complexes obtained in this way are compounds containing the lactam compound or salt thereof in the above invention and a metal atom.

The above metal atom is not particularly limited and example thereof includes magnesium (Mg), calcium (Ca), iron (Fe), manganese (Mn), zinc (Zn), molybdenum (Mo), copper (Cu), and the like. Of these, iron and copper are preferred, and iron is particularly preferred. Iron complex is suitable as an iron supply material for plants in cultivation using foliar spraying and hydroponics.

A coordination state of the metal atom in the complex of the present invention is not particularly limited. It is usually in a state of metal ion (monovalent, divalent, trivalent, etc.), but it may also be in a state of zero-valent metal. The number of the metal atom included may be only one, or be two or more.

In the present invention, the lactam compound or its salt and the complex are suitable as raw material components for a fertilizer or a plant growth regulator.

The fertilizer and plant growth regulator in the present invention are composed of the lactam compound or its salt and/or the complex, and other compositions suitable for the agricultural field may further be applied. The other compositions are exemplified below.

(1) Only lactam compound or its salt and/or complex;
(2) Aqueous solution of lactam compound or its salt and/or complex;
(3) Mixture consisting of lactam compound or its salt and/or complex, and other compounds; and
(4) Aqueous solution or aqueous dispersion containing a lactam compound or its salt and/or complex, other compounds, and water.

In the above configurations (2) and (4), pH of the solution is not particularly limited, but is preferably in a range from 1 to 7, and more preferably from 2 to 5.

In these cases, a (total) concentration of the lactam compound or its salt and/or the complex is preferably in a range from 10% to 50% by mass, and more preferably from 10% to 30% by mass based on a total liquid from viewpoints of workability and the effect obtained.

In the above configurations (3) and (4), the other compounds may be either inorganic or organic compounds.

Examples of the inorganic compound include a magnesium compound such as magnesium hydroxide and magnesium chloride; a calcium compound such as calcium hydroxide, calcium carbonate and calcium chloride; an iron compound such as iron sulfate, iron nitrate, iron oxide ($Fe_2O_3$), ferric chloride ($FeCl_3$) or hydrate thereof; a manganese compound such as manganese dioxide, manganese sulfate pentahydrate, and manganese chloride tetrahydrate; a boron compound such as sodium tetraborate 10 hydrate and boric acid; a zinc compound such as zinc sulfate and zinc oxide; a molybdenum compound such as sodium molybdate and ammonium molybdate; a copper compound such as copper sulfate and copper nitrate; and the like. Of these, an iron compound is preferred. This iron compound may be either divalent or trivalent.

Examples of the organic compound include a metal salt of EDTA, a metal-EDTA complex, a metal-EDDHA complex, a metal-EDPA complex, proteins, a pesticide active material, sugars, a surfactant (emulsifiers, defoamers, dispersants, etc.), and the like. Anionic, cationic, nonionic, and amphoteric surfactants may be used as the surfactant.

In the above configuration (4), when a surfactant is contained, a content ratio of the surfactant is preferably in a range from 0.00001 to 1 part by mass, and more preferably from 0.01 to 0.1 part by mass based on 100 parts by mass of a total of the lactam compound and/or the complex.

The fertilizer and plant growth regulator in the present invention are suitable for cultivation using foliar spraying and hydroponics. It is also suitable for plant growth in alkaline soils.

Plants have an ability to absorb nutrients not only from roots but also from the surface of leaves, stems, and fruits. Therefore, foliar application of fertilizer and plant growth regulator in liquid state leads to a nutrient supply effect.

In the hydroponics, the flow method (NFT, DFT), static method, etc., which are publicly known, may be applied.

EXAMPLES

Hereinafter, the present invention is specifically described by way of Examples. The present invention is not limited to the Examples.

Example 1

One gram of the following compound (hereinafter, referred to as "PDMA") that is represented by the following formula (11) and is obtained by a method described in WO 2017/082111 was dissolved in 1M hydrochloric acid aqueous solution, and concentration was then conducted to form a hydrochloride salt. Next, the hydrochloride salt was dissolved in 190 mL of water, and the resulting solution was heated to a temperature of 70° C., and stirred for two hours to obtain the following lactam compound (L1) having a hydrochloride type in an amount of 1 gram.

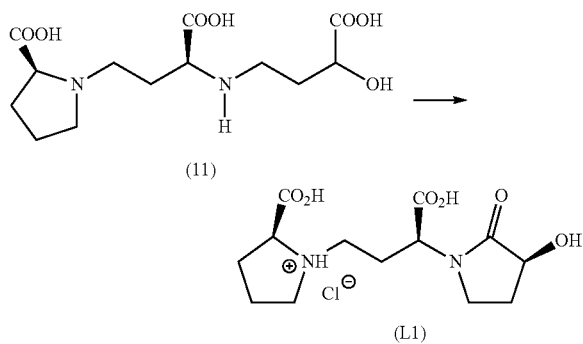

Data of $^1$H-NMR spectra of the resulting hydrochloride type lactam compound (L1) is as follows.

$^1$H NMR (400 MHz, D$_2$O): δ 4.45 (dd, J=9.4, 5.5 Hz, 1H), 4.35 (t, J=8.4 Hz, 1H), 4.08 (dd, J=9.4, 7.0 Hz, 1H), 3.68 (ddd, J=11.3, 7.2, 4.0 Hz, 1H), 3.36-3.22 (m, 3H), 3.14-2.97 (m, 2H), 2.45-2.24 (m, 3H), 2.23-2.09 (m, 1H), 2.09-1.07 (m, 2H), 1.95-1.68 (m, 2H).

After that, the hydrochloride type lactam compound (L1) was purified using a cation exchanging resin "DOWEX™ 50WX8" (product name) and developing solvent (from H$_2$O to 5% ammonia aqueous solution) to obtain the following lactam compound (L2).

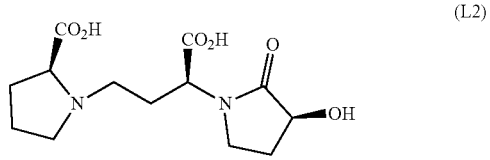 [SMILES: O=C(O)[C@@H]1CCCN1CC[C@@H](C(=O)O)N1CC[C@H](O)C1=O]

Data of $^1$H-NMR spectra of the resulting lactam compound (L2) is as follows.

$^1$H NMR (500 MHz, D$_2$O): δ 4.35 (t, J=8.7 Hz, 1H), 4.24 (dd, J=9.1, 6.0 Hz, 1H), 3.84 (dd, J=9.3, 6.5 Hz, 1H), 3.67 (ddd, J=10.6, 6.5, 3.8 Hz, 1H), 3.34-3.18 (m, 3H), 3.06-2.91 (m, 2H), 2.45-2.29 (m, 2H), 2.29-2.18 (m, 1H), 2.06-1.92 (m, 3H), 1.90-1.77 (m, 2H).

Hereinafter, various evaluations were carried out using the above-mentioned lactam compound (L2).

(A) Stability of Aqueous Solution

In order to investigate the stability of the lactam compound (L2) in water having different pH, an aqueous solution having a pH of 1 using hydrochloric acid, an aqueous solution having a pH of 7 in which the lactam compound (L2) was dissolved in water, and an aqueous solution having a pH of 9 using sodium hydrogen carbonate were subjected to $^1$H-NMR measurement. The results are shown in FIG. 1. It can be seen, from FIG. 1, that the lactam ring structure is maintained although the peak shift is observed in the $^1$H-NMR spectrum.

(B) Foliar Spraying Test

Figure 2:
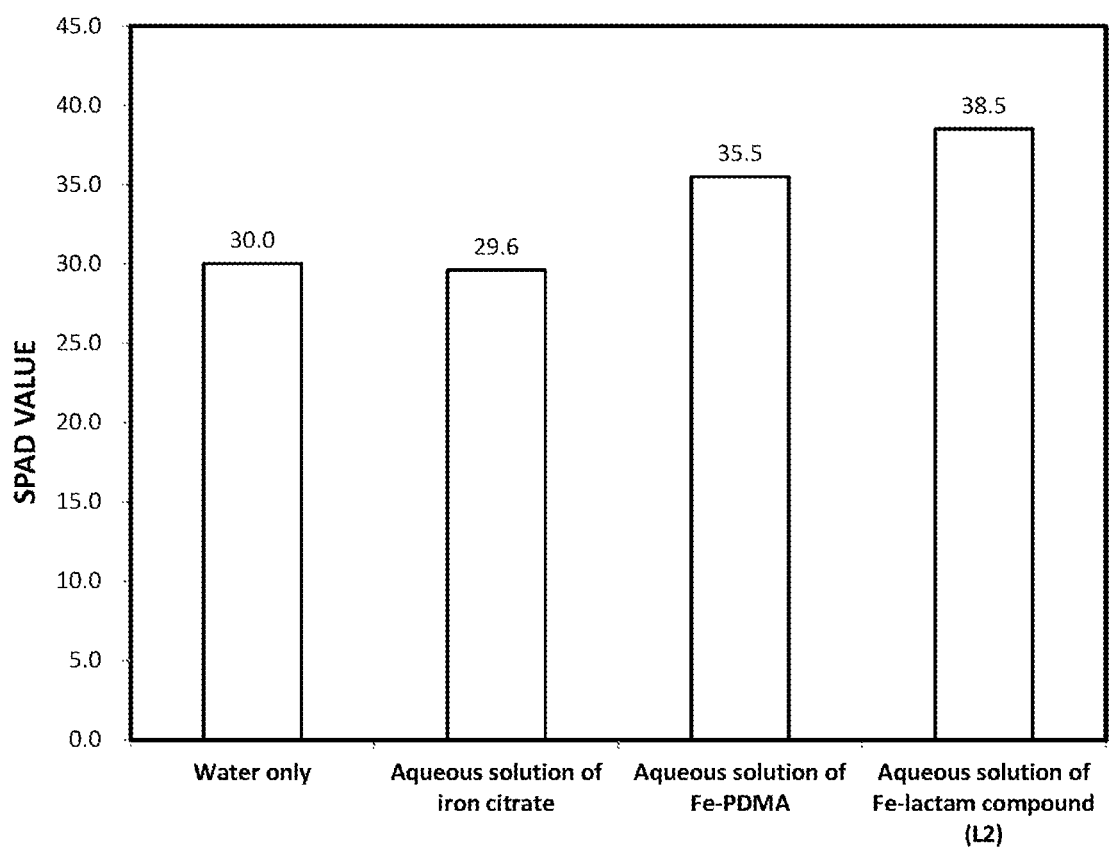
FIG. 2 is a graph showing results of the foliar spraying test.

Komatsuna seeds were seeded in a nursery soil "Hana-chan nursery soil" (trade name) manufactured by Hana-gokoro Co., Ltd., and cultivation was started in a greenhouse with natural sunlight. On the 8th day, we thinned out so that their grow would be aligned. After thinning, on the 10th, 12th, 14th, 17th, 19th and 21st days, 10 mL of water and aqueous solutions containing 20 μmol of each of iron citrate, a complex composed of PDMA and iron sulfate (III) (hereinafter, referred to as "Fe-PDMA"), or a complex composed of the lactam compound (L2) and iron sulfate (III) (hereinafter, referred to as "Fe-lactam compound (L2)") were used in an amount of 10 mL to conduct foliar application. The aqueous solutions are prepared by diluting 1,000-fold with a surfactant "Dyne" (trade name) manufactured by Sumitomo Chemical Garden Products Inc., and have pH of 4 to 5. SPAD values were measured 24 days later (3 days after the spraying was completed). The results are shown in FIG. 2. It is found from FIG. 2 that when the Fe-lactam compound (L2) was used, superior growth effect was obtained when iron citrate or Fe-PDMA was sprayed on the foliage compared to when only water was sprayed.

(C) Hydroponic Cultivation Test

Figure 3:
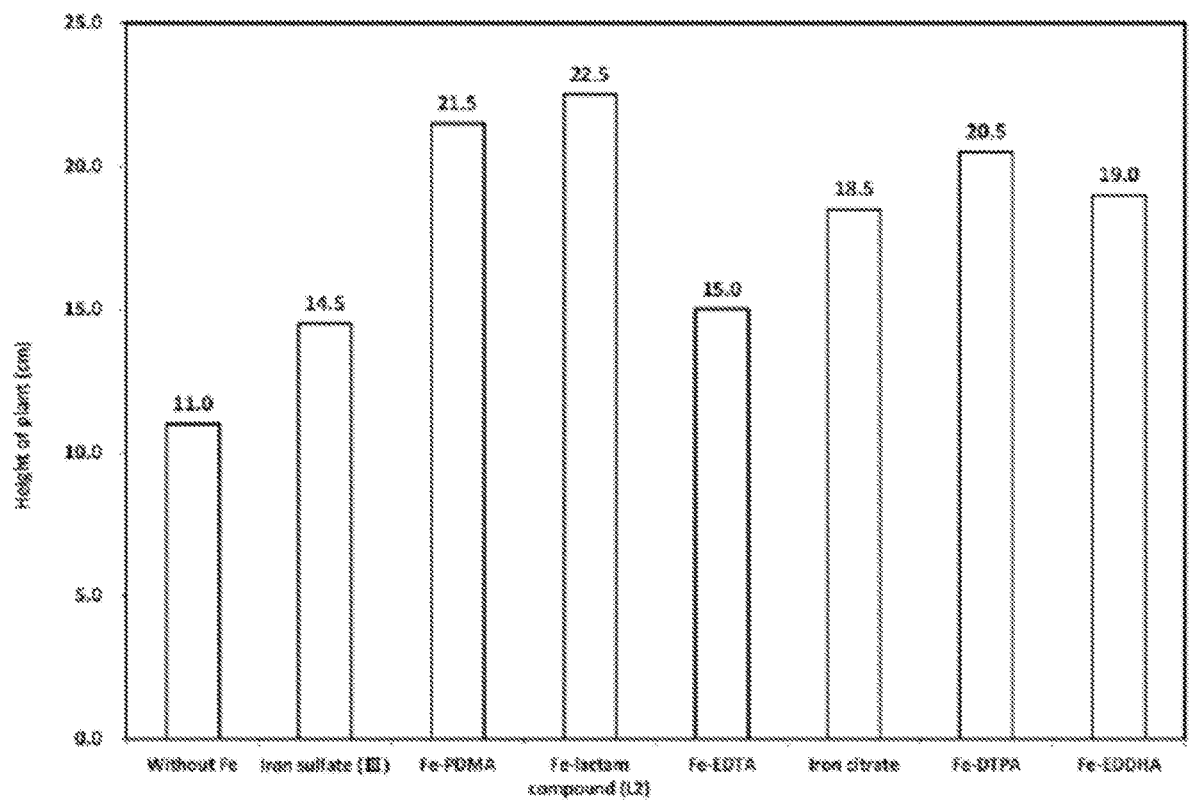
FIG. 3 is a graph showing results of the hydroponic cultivation test.

The paddy rice variety "Nipponbare" was seeded in tap water. When roots and buds emerged, seedlings were soaked in a hydroponic solution (formulation in the Horticultural Experiment Station). On the 8th day after sowing, the seedlings were transplanted into a hydroponic solution of a formulation in the Horticultural Experiment Station (without iron). Aqueous solutions of iron sulfate (III), Fe-PDMA, Fe-lactam compound (L2), Fe-EDTA, iron citrate, Fe-DTPA or Fe-EDDHA were further added to each of the hydroponic solution as 90 μM only once to measure plant heights 7 days after the administration. The results are shown in FIG. 3. It is found from FIG. 3 that when the Fe-lactam compound (L2) was used, the growth of the paddy rice was remarkably promoted and superior growth effect was obtained when other aqueous solutions of iron citrate or Fe-PDMA were administered.

(D) Alkaline Soil Cultivation Test

Figure 4:
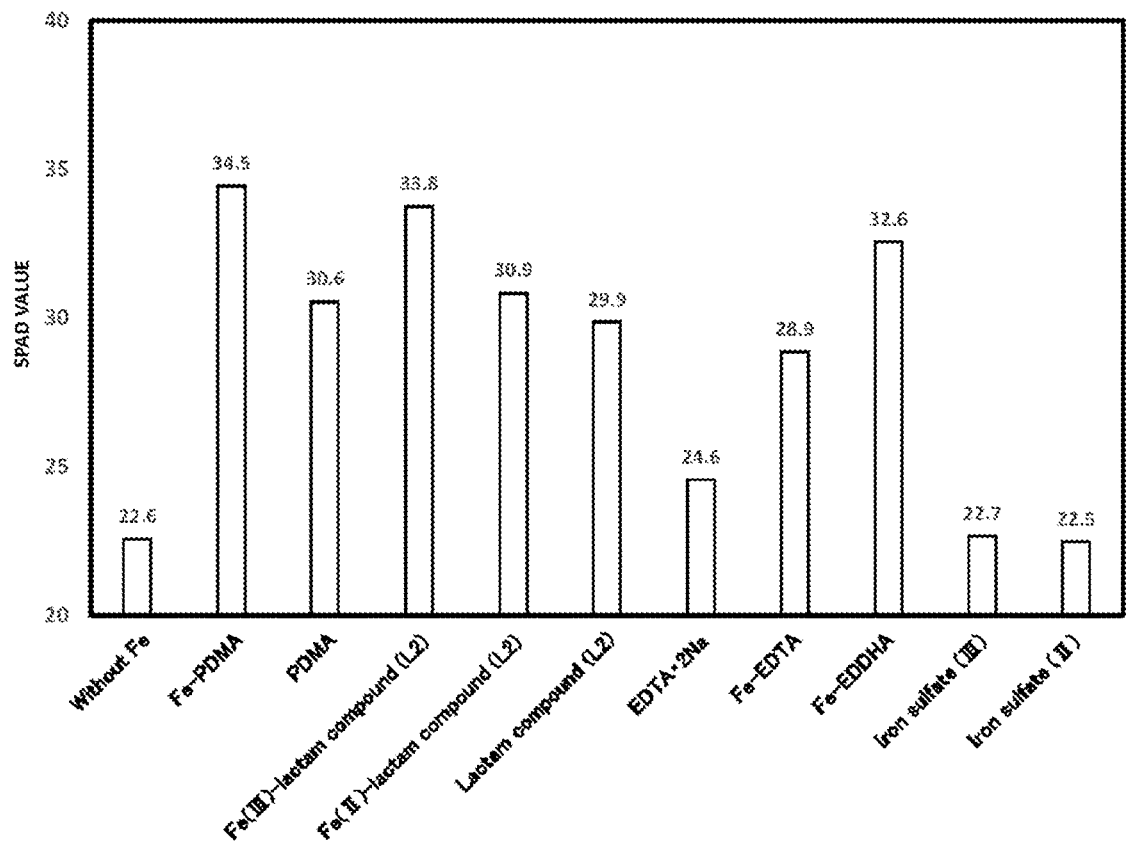
FIG. 4 is a graph showing results of the alkaline soil cultivation test.

The paddy rice variety "Nipponbare" was seeded in tap water. When roots and buds emerged, seedlings were soaked in a hydroponic solution (formulation in the Horticultural Experiment Station). When the plant height reached about 7 cm, the seedlings were transplanted into fossil shellfish soil having a pH9. Aqueous solutions containing 30 μmol of each of Fe-PDMA, only PDMA, a complex composed of the lactam compound (L2) and iron sulfate (III) (hereinafter, referred to as "Fe(III)-lactam compound (L2)"), a complex composed of the lactam compound (L2) and iron sulfate (II) (hereinafter, referred to as "Fe(II)-lactam compound (L2)"), lactam compound (L2), disodium ethylenediamine tetraacetate, Fe-EDTA, Fe-EDDHA, iron sulfate (III) or iron sulfate (II). were administered only once to each of the soil to measure SPAD values 7 days after the administration. The results are shown in FIG. 4. According to FIG. 4, SPAD values were 33.8 and 30.9, respectively when either the Fe-lactam compound (L2) of divalent and trivalent iron was used. It is found that the growth effect can be obtained even in alkaline soil by administering the lactam compound of the present invention. Moreover, not only the effect can be obtained with the lactam compound (L2) as it is, but further effect can be expected if a complex with Fe and a lactam compound are used.

INDUSTRIAL APPLICABILITY

The lactam compound and salt of the present invention, and complex of the present invention are useful in a fertilizer for plant growth, a plant growth regulating agent, and the like.

The invention claimed is:

1. A lactam compound and a salt thereof, represented by general formulae (1) and (2):

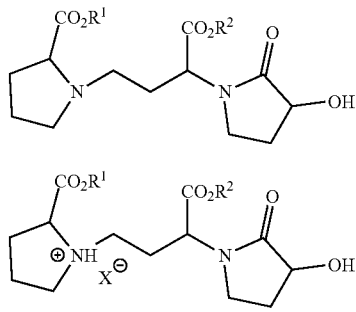

wherein $R^1$ and $R^2$ may be the same or different, and each represent a hydrogen atom, a protective group of a carboxyl group or a cation, and $X^-$ is a halogen ion, an organic acid ion, or an inorganic acid ion.

2. The lactam compound and a salt thereof according to claim 1, wherein $R^1$ and $R^2$ in the general formulae (1) and (2) are hydrogen atoms.

3. The lactam compound and a salt thereof according to claim 1, wherein $R^1$ and $R^2$ in the general formulae (1) and (2) are protective groups of a carboxyl group, and the protective group is a methyl group or an ethyl group.

4. The lactam compound and a salt thereof according to claim 1, which is represented by general formulae (3) or (4):

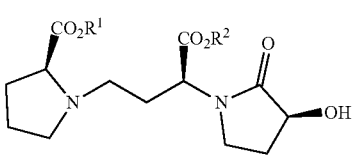

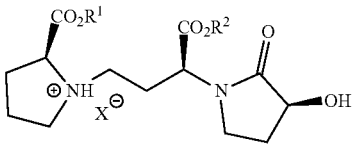

wherein $R^1$ and $R^2$ may be the same or different, and each represent a hydrogen atom, a protective group of a carboxyl group or a cation, and $X^-$ is a halogen ion, an organic acid ion, or an inorganic acid ion.

5. A complex comprising the lactam compound or salt thereof according to claim 1, and a metal atom.

6. The complex according to claim 5, wherein the metal atom is an iron.

7. A fertilizer comprising the lactam compound or salt thereof according to claim 1.

8. A plant growth regulating agent comprising the lactam compound or salt thereof according to claim 1.

* * * * *